United States Patent
Pribanic et al.

(10) Patent No.: US 11,776,669 B2
(45) Date of Patent: *Oct. 3, 2023

(54) SYSTEM AND METHOD FOR SYNTHETIC INTERACTION WITH USER AND DEVICES

(71) Applicant: MedRespond, Inc., Pittsburgh, PA (US)

(72) Inventors: Virginia Flavin Pribanic, McKeesport, PA (US); Alexander Hauptmann, Finleyville, PA (US)

(73) Assignee: MedRespond, Inc., Pittsburgh, PA (US)

(*) Notice: Subject to any disclaimer, the term of this patent is extended or adjusted under 35 U.S.C. 154(b) by 96 days.

This patent is subject to a terminal disclaimer.

(21) Appl. No.: 17/349,395

(22) Filed: Jun. 16, 2021

(65) Prior Publication Data

US 2021/0313019 A1 Oct. 7, 2021

Related U.S. Application Data

(63) Continuation of application No. 15/795,238, filed on Oct. 26, 2017, now Pat. No. 11,074,994.

(Continued)

(51) Int. Cl.
*G16H 10/20* (2018.01)
*G16H 20/30* (2018.01)
(Continued)

(52) U.S. Cl.
CPC ............. *G16H 10/20* (2018.01); *G06F 40/40* (2020.01); *G06N 3/08* (2013.01); *G06N 5/046* (2013.01);
(Continued)

(58) Field of Classification Search
CPC ........ G16H 10/20; G16H 20/30; G16H 10/60; G16H 20/10
See application file for complete search history.

(56) References Cited

U.S. PATENT DOCUMENTS

| 3,747,069 A | 7/1973 | Herschberg |
|---|---|---|
| 4,917,108 A | 4/1990 | Mault |

(Continued)

FOREIGN PATENT DOCUMENTS

| JP | 2003-186995 | 7/2003 |
|---|---|---|
| JP | 2008-102699 A | 5/2008 |

(Continued)

OTHER PUBLICATIONS

Jiang, Lu, MemexQA: Visual Memex Question Answering; arXiv:1708.01336; Aug. 4, 2017, pp. 1-10.

(Continued)

*Primary Examiner* — Jay M. Patel
(74) *Attorney, Agent, or Firm* — METZ LEWIS BRODMAN MUST O'KEEFE, LLC

(57) ABSTRACT

Systems and methods for conducting automated synthetic interactions with a user, such as a patient at home following a medical procedure. A digital coach having a processor and memory initiates a session with a user's interactive device, and presents pre-recorded scripts as video and/or audio through the interactive device. The user's responses are received by the digital coach through the interactive device. Peripheral devices, such as medical devices, may be used by the user or controlled by the digital coach to obtain data measurements regarding the physiological condition of the user. The processor of the digital coach analyzes the data from the user responses and devices, and semantically interprets the responses and data to determine the next action and script to present the user in the session. The digital coach provides a conversational, dynamic, adaptive session with a user based on semantically expanded interpretations of data by the processor.

20 Claims, 9 Drawing Sheets

Related U.S. Application Data

(60) Provisional application No. 62/413,112, filed on Oct. 26, 2016.

(51) Int. Cl.

| | |
|---|---|
| *G16H 10/60* | (2018.01) |
| *G16H 20/10* | (2018.01) |
| *G06N 20/00* | (2019.01) |
| *G16H 50/20* | (2018.01) |
| *G16H 40/67* | (2018.01) |
| *G16H 70/20* | (2018.01) |
| *G06N 5/046* | (2023.01) |
| *G06N 3/08* | (2023.01) |
| *G06F 40/40* | (2020.01) |

(52) U.S. Cl.
CPC ............. *G06N 20/00* (2019.01); *G16H 10/60* (2018.01); *G16H 20/10* (2018.01); *G16H 20/30* (2018.01); *G16H 40/67* (2018.01); *G16H 50/20* (2018.01); *G16H 70/20* (2018.01)

(56) References Cited

U.S. PATENT DOCUMENTS

| | | |
|---|---|---|
| 5,038,792 A | 8/1991 | Mault |
| 5,178,155 A | 1/1993 | Mault |
| 5,179,958 A | 1/1993 | Mault |
| 5,836,300 A | 11/1998 | Mault |
| 5,870,755 A | 2/1999 | Stevens |
| 6,135,107 A | 10/2000 | Mault |
| 6,468,222 B1 | 10/2002 | Mault |
| 6,478,736 B1 | 11/2002 | Mault |
| 6,513,532 B2 | 2/2003 | Mault |
| 6,527,711 B1 | 3/2003 | Stivoric |
| 6,571,200 B1 | 5/2003 | Mault |
| 6,595,929 B2 | 7/2003 | Stivoric |
| 6,605,038 B1 | 8/2003 | Teller |
| 6,610,012 B2 | 8/2003 | Mault |
| 6,790,178 B1 | 9/2004 | Mault |
| 7,020,508 B2 | 3/2006 | Stivoric |
| 7,149,756 B1* | 12/2006 | Schmitt ................. G16H 50/20 |
| 7,153,262 B2 | 12/2006 | Stivoric |
| 7,261,690 B2 | 8/2007 | Teller |
| 7,285,090 B2 | 10/2007 | Stivoric |
| 7,502,643 B2 | 3/2009 | Farringdon |
| 7,689,437 B1 | 3/2010 | Teller |
| 7,941,323 B2 | 5/2011 | Brown |
| 8,193,931 B2 | 6/2012 | Rapaport |
| 8,219,502 B2 | 7/2012 | Gold |
| 8,398,546 B2 | 3/2013 | Pacione |
| 8,630,867 B2 | 1/2014 | Yoo |
| 9,123,083 B2 | 9/2015 | Brown |
| 2001/0029340 A1 | 10/2001 | Mault |
| 2001/0044581 A1 | 11/2001 | Mault |
| 2001/0044588 A1 | 11/2001 | Mault |
| 2001/0049470 A1 | 12/2001 | Mault |
| 2002/0007286 A1 | 1/2002 | Okamoto |
| 2002/0010596 A1 | 1/2002 | Matory |
| 2002/0027164 A1 | 3/2002 | Mault |
| 2002/0028995 A1 | 3/2002 | Mault |
| 2002/0055857 A1 | 5/2002 | Mault |
| 2002/0062069 A1 | 5/2002 | Mault |
| 2002/0109600 A1 | 8/2002 | Mault |
| 2002/0133378 A1 | 10/2002 | Mault |
| 2003/0152607 A1 | 8/2003 | Mault |
| 2003/0208113 A1 | 11/2003 | Mault |
| 2004/0111479 A1* | 6/2004 | Borden ................... H04L 51/04 709/206 |
| 2006/0085225 A1* | 4/2006 | Gold ...................... G16H 10/20 705/2 |
| 2006/0161457 A1* | 7/2006 | Rapaport ............... G16H 10/20 705/2 |
| 2006/0200007 A1* | 9/2006 | Brockway .............. G16H 40/67 128/920 |
| 2010/0179833 A1 | 7/2010 | Roizen et al. |
| 2011/0295615 A1 | 12/2011 | Bengtson |
| 2013/0085768 A1 | 4/2013 | Brown |
| 2014/0257836 A1 | 9/2014 | Walker et al. |
| 2017/0256259 A1* | 9/2017 | Froelich .................. G10L 15/04 |

FOREIGN PATENT DOCUMENTS

| | | |
|---|---|---|
| JP | 2010-088890 | 4/2010 |
| JP | 2010-057552 | 6/2013 |
| JP | 2016-134132 A | 7/2016 |
| KR | 10-2010-0039705 | 10/2016 |

OTHER PUBLICATIONS

Hauptmann, Alexander, Quarterly Progress Report—Monitoring and Coaching to Promote Proper Inhaler Technique project; pp. 1-12; Carnegie Mellon University, Pittsburgh, Pennsylvania.

International Searching Authority; International Search Report and Written Opinion of the International Searching Authority; International Application No. PCT/US17/58627; Patent Cooperation Treaty; pp. 1-12; publisher United States International Searching Authority; Published Alexandria, Virginia, US; copyright and dated Jan. 5, 2018; (12 pages).

European Patent Office, Communication Pursuant to Article 94(3) EPC, Communication regarding European Application No. 17865160.0; pp. 1-11, publisher European Patent Office, published Rijswijk, The Netherlands, copyright and dated May 6, 2020; (11 pages).

Japanese Intellectual Property Office; Office Action; English Translation of Office Action regarding JP Patent Application No. JP2019-544788; pp. 1-8; publisher Japanese Intellectual Property Office; published Tokyo, Japan; copyright and dated Nov. 22, 2021; (8 pages).

* cited by examiner

SYSTEM AND METHOD FOR SYNTHETIC INTERACTION WITH USER AND DEVICES

CLAIM OF PRIORITY

The present application is a continuation of co-pending U.S. patent application Ser. No. 15/795,238, filed on Oct. 26, 2017, which claims priority to U.S. Provisional Application Ser. No. 62/413,112 filed on Oct. 26, 2016, the contents of all of which are incorporated herein by reference in their entireties.

FIELD OF THE INVENTION

This invention relates to telemedicine and telehealth monitoring. More particularly, this invention relates to systems patients can use to monitor their post-operative or post-treatment recovery and manage interactions with medical devices in connection therewith. The invention also relates to data interpretation and analysis.

BACKGROUND

Following medical treatment or surgery, there is often a recovery period during which the patient heals and regains their strength and stamina. While an initial recovery period may be spent in the treating physician's office or hospital, this initial period of observation by medical personnel is only required to make sure the patient is stable. Once stable, the patient is released to go home, but the recovery process has only just begun. Depending on the procedure or treatment, as well as the patient's age and general health, the recovery time can be anywhere from a few days to a few months. Multiple follow-up appointments with the health service provider may be required to assess progress of the recovery. These appointments must be scheduled, and the patient must travel to and from the appoint at an office or hospital. If the recovery is not going well, this travel may be uncomfortable, painful, or even dangerous for the patient. Home visitations, such as by a nurse practitioner, are not always possible due to heavy workloads on medical staff. Telephone follow-ups by medical staff rely on patient self-assessment and reporting, which are highly subjective, may differ from medical standards, and could be unreliable if the patient fails to report all the relevant information or doesn't know how to explain what they are experiencing.

At-home monitoring of the patient during their recovery is therefore desired, if possible, but accurate information must be obtained, and the health service provider must be notified of significant changes. However, if the recovery goes well, simple monitoring is all that may be needed, along with assurances to the patient that they are on track. Medical personnel may not be required for such monitoring, but accurate information must still be obtained. Similarly, patients with chronic conditions such as diabetes or COPD may need to monitor their health over a period of time, which may not rise to the level of requiring medical attention.

Advancements in telemedicine, such video-conferencing with a medical professional for basic evaluation, have now become options available to patients. With such technology-assisted remote medical evaluations, the patient does not have to leave their home. Scheduled appoints are often not required, or may be obtained the same day as requested. However, these remote interactions are limited in the ability of the medical professional to see and assess the patient's medical condition. They are limited to whatever devices the patient may have at their disposal to obtain information, such as a scale or glucometer. Additional information may be needed, such as from medical devices that the patient does not have access to, or from lab tests that the patient must have performed elsewhere. Often, the medical personnel staffing such telemedicine are nurse practitioners or general practitioners, and do not have specialized expertise in all areas of medicine. Therefore, it would be beneficial for patients to have a way of monitoring their recovery at home, in an accurate way, and which can handle nuanced or personalized questions specific to that patient.

Automated systems could provide some relief, and can handle large amounts of information. However, automated interactions are pre-recorded and follow a predetermined path that contemplate only certain limited responses. Any deviations from this path cannot be accommodated by an automated system. Advancements have been made in automated systems as well, such as with synthetic interviews as described in U.S. Pat. No. 5,870,755 to Stevens et al., which is incorporated by reference herein in its entirety. Such synthetic interviews provide a conversational interview between an avatar and a person, based on natural language responses from the person. The questions to be posed and possible corresponding answers are reversed indexed based on context and syntax to determine relationships between words. This enables the synthetic interview system to incorporate responses from the person that are not in an expected form. Such systems, however, are limited to analysis of words having known rules of language, grammar and syntax. They still cannot address more complex and nuanced situations.

There remains a need, therefore, for an at-home monitoring system that a patient can use during recovery or any monitoring period, in which any circumstance can arise and be addressed. Such a system would have to be both extensive and accurate, and be able to handle unknown circumstances.

SUMMARY OF THE INVENTION

Systems and methods for automated synthetic sessions with users and devices are disclosed. The system includes a digital coach having a processor and memory that coordinates the presentation of scripts, such as videos, to a patient or user, providing instructions and prompting the collection of information. The digital coach may also provide operative instructions to various peripheral devices, such as medical devices that are in proximity to the patient, to control the devices and collect data and information from the devices regarding the physiological status and conditions of the patient. The digital coach semantically analyzes and interprets the user responses and data from medical devices to determine the next appropriate action, which may include choosing the next script to be presented to the user. These steps are repeated, forming a session that is an iterative process or feedback loop where information and data is collected and analyzed at each step, semantic relationships are contextually determined and considered in interpreting the data, which then informs and directs the next step in the session. The session may be multi-modal, such as including video, audio, text, and digital information. Further, the interactions in each session may be translated into any language, including sign language.

The digital coach and user interact through a connection, such as an Internet connection. The user utilizes an interactive device, such as a computer, tablet, smartphone or similar device to participate in the session with the digital coach.

The various scripts the digital coach presents to the user are displayed on the display of their interactive device or delivered via the device's speakers, and the built-in speakers, microphone and camera can be used to record the user's responses. The user's responses are converted to digital signals that are processed as data by the digital coach. Information collected from peripheral devices, such as medical devices, are transmitted to the digital coach, converted and processed as data. The data can be qualitative or quantitative in nature.

The digital coach includes a processor and memory. The processor includes an analyzer that transforms the data at each step into assessments of that data. The analyzer accesses knowledge bases and compares the data to predefined reference points to classify each piece of data into a category. Various knowledge bases, classifications and reference points are stored in the memory for access during processing. The data as modified by the classification or category define an assessment. An action engine of the processor then semantically expands each assessment by associating each assessment with various additional pieces of information that are contextually related to or correlate to the assessment. This forms interpretations, which are strings of data and semantically related information. Multiple interpretations of the data result. The memory also stores knowledge bases of correlations and indexed information to access and cross-reference in semantically expanding the assessments. The action engine of the processer then identifies and applies the most appropriate rule to each interpretation, generating possible actions. The rules may be included in the memory, or may be neural networks or other machine learning system that improves accuracy over time. Multiple possible actions are generated, and are weighted, ranked, or prioritized. The processor chooses the most appropriate action of the possible actions, and issues instructions to the user and/or medical devices to obtain further information or instruction. The processor may also send instructions, alerts, notifications, requests, or other communication to others such as the health service provider (HSP), electronic health record (EHR) of the patient, or third party such as a laboratory performing testing or a pharmacy. The instructions with respect to a user are instructions to present an identified script as the next script to the user.

Therefore, the sessions between the digital coach do not follow a pre-established script, but rather depend at each step on the user's responses and data from various peripheral and medical devices provided in previous steps. The session is truly interactive, and no two sessions will be the same. This type of interaction is possible because the processor semantically expands all incoming data. Contextual interpretation of words, for example, is known. However, analogous techniques have not been applied to data since it is vastly more complex and requires many more factors to consider.

The systems and methods, together with their particular features and advantages, will become more apparent from the following detailed description and with reference to the appended drawings.

DESCRIPTION OF THE DRAWINGS

Like reference numerals refer to like parts throughout the several views of the drawings.

DETAILED DESCRIPTION

As shown in the accompanying drawings, the present invention is directed to systems and methods for conducting an automated synthetic interaction with a user, such as a patient at home following a medical procedure, that utilizes peripheral devices such as medical devices to collect data about the physiological condition of the patient. The automated synthetic interaction, or session, is conducted by a digital coach that adaptively interacts with the patient to monitor their recovery and overall health, and coordinates data from both the patient and various peripheral devices. The digital coach may also send operative instructions to the various devices to control them and initiate data collection and/or transmission. The digital coach semantically analyzes the input and data from the patient and devices, and interprets the input and data to determine the next course of action in the session. The digital coach then directs the next course of action, which can be further questions or answers to the patient and/or directing data collection from devices for additional information. The cycle then repeats, forming a feedback loop and iterative process.

Figure 1:
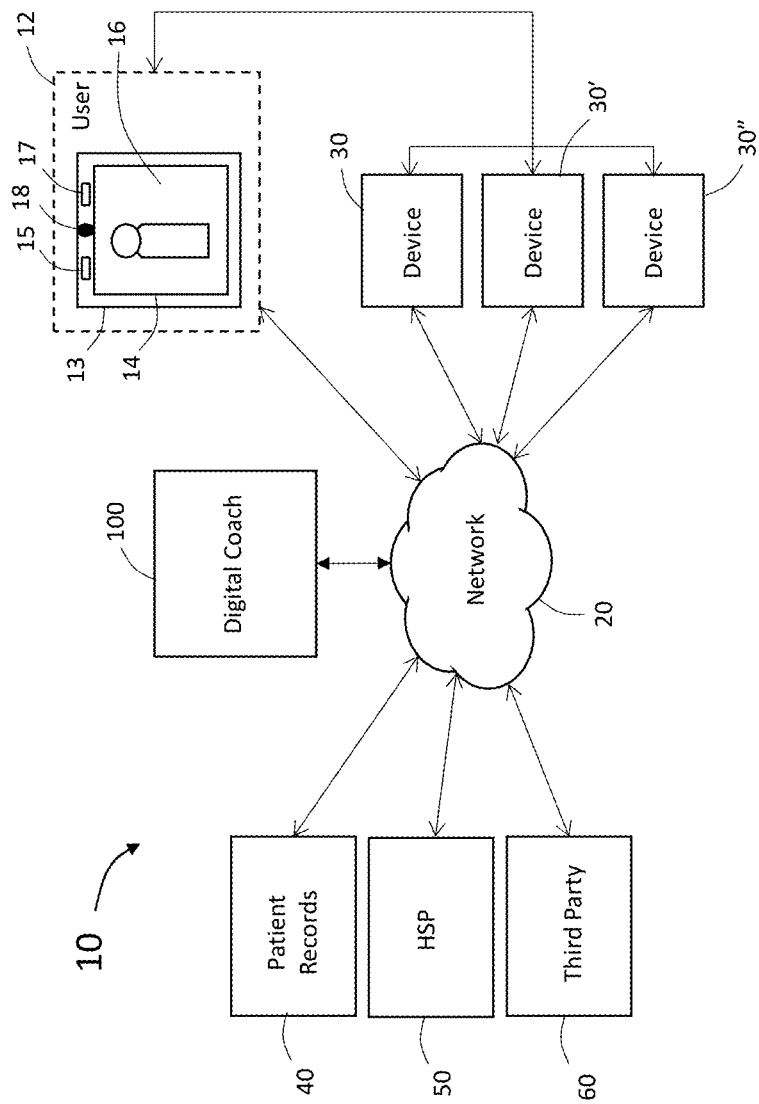
FIG. 1 is a schematic diagram of one embodiment of the system of the present invention.

As shown in FIG. 1, the system 10 includes a digital coach 100 that performs the interviews, controls the devices, analyzes and interprets the data and information, and decides the next course of action. In a preferred embodiment, the digital coach 100 is hosted electronically in the cloud, and thus is accessible through the network 20. The user 12 interacts with the digital coach 100 through an interactive device 13 in proximity to the user 12, such as a computer, laptop, tablet, mobile device, smart device, phone, watch, speaker device, or other computing device. Preferably, the interactive device 13 is a personal computing device, and need not be a specialized piece of equipment. The digital coach 100 is in electronic communication with the interactive device 13 and may present to the user 12 through the interactive device's interface, such as the display 14 for visual presentation and speakers 15 for auditory presentation associated with videos. The interactive device 13 may also include an input 16, which may be a keyboard, touch pad, touch-enabled screen with soft keys, or other structure for entry of information to the interface. The interactive device 13 may also include a microphone 17 to pick up sounds associated with a patient's verbal responses to the digital coach 100, as well as a camera 18 to monitor and/or record video of the patient. These various components of the interactive device 13 may come as part of the device 13, or may optionally be attached to the device, such as a separate keyboard with physical keys. However, use of the interactive device 13 with the digital coach 100 need not require modifications to a patient's own personal cell phone, laptop, tablet or computer. A user 12 may be able to access the digital coach 100 through a website available on the network 20, such as the Internet, preferably with secure login information. In some embodiments, however, the digital coach 100, or at least a portion thereof, may be installed on the user's own personal interactive device 13 to facilitate session, such as when access to the network 20 may be limited or unavailable.

The term "digital coach" is used for ease of discussion, since it interacts with the user 12 in an accessible, natural feeling way that invokes the feeling of having a conversation with a person. It will become clear from the remainder of the disclosure, however, that the digital coach 100 is a computer-implemented software or application which may be installed on a computing device and may be hosted in a remote location, such as on a server 80 that is accessible through the network 20 or other Internet connection. In some embodiments, however, the digital coach 100 may be installed on the user's interactive device 13 and may operate, at least in part, locally. In still other embodiments, an operative program and a cache of information may be stored locally on the interactive device 13, and may coordinate through the network 20 or Internet for complete access to the remainder of the total information comprising the digital coach.

In at least one embodiment, the user 12 may be a person who has received medical treatment that requires follow-up monitoring, such as an operation, or who will receive medical treatment that requires preparation prior to treatment. Accordingly, the terms "user" and "patient" may be used interchangeably throughout this disclosure. In some embodiments, user 12 may refer to a caregiver or other individual assisting the patient, such as a family member or in-home care provider. The caregiver may interact with the digital coach 100 with or in place of the patient, to assist the patient or in cases where the patient is not able to participate themselves. In additional embodiment, the user 12 may be a person who is in need of long-term health monitoring, such as for a chronic condition like diabetes or a cancer patient. The digital coach 100 may therefore also provide interactive health monitoring in general, in addition to pre-operative, post-operative, or surrounding specific medical procedures.

Figure 2:
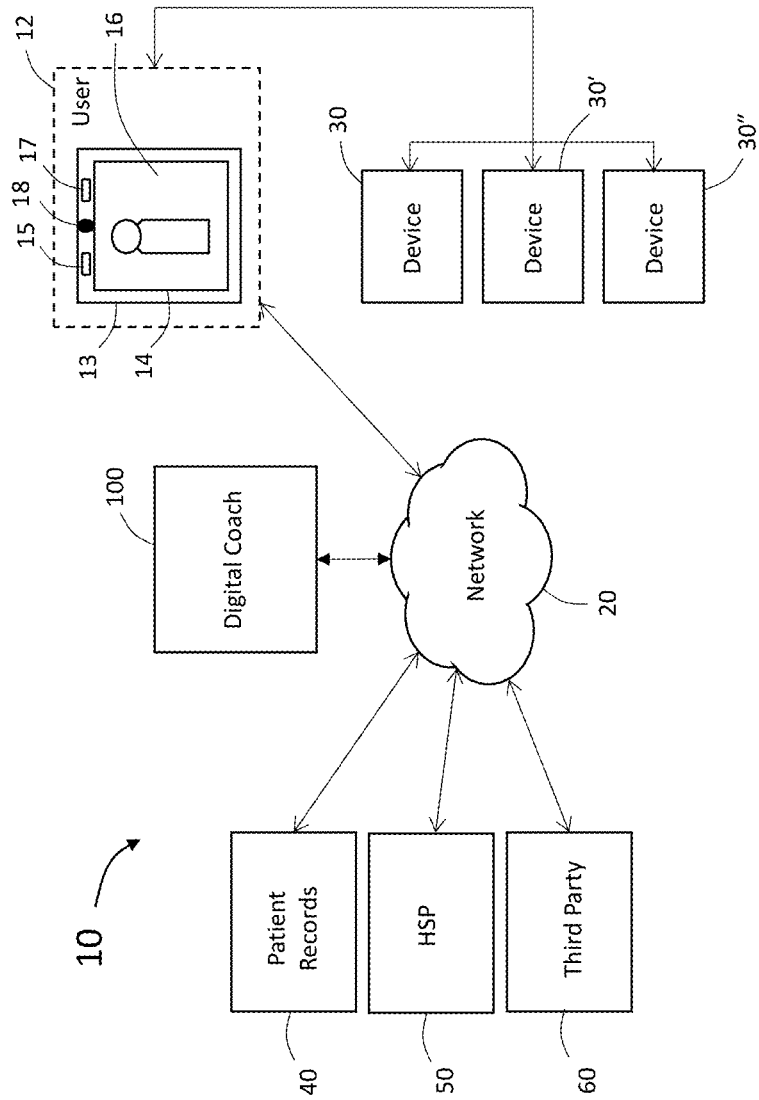
FIG. 2 is a schematic diagram of a second embodiment of the system.

The digital coach 100, or at least the processor 110 thereof, may also be in electronic communication with and interact with various peripheral devices 30, 30', 30" that the user 12 has at their disposal. In a preferred embodiment, these devices 30 may be medical devices that are designed to collect physiological data about the patient relative to a medical or health condition. As used herein, a "medical device" is any device that collects data indicative of a physiological condition of the patient, and may be classified as a medical device according to Tile 21 of the Code of Federal Regulations (CFR), Parts 862-892, or may be any device that is governed by the FDA as a medical device. For example, medical devices 30 may include, but are not limited to, thermometers, blood pressure cuffs, pulse oximeters, stethoscopes, glucometers, ECG or EKG devices, galvanic skin response sensors, diaphoretic sensors, electrolyte sensors, spirometers and the like. However, other peripheral devices 30 that provide data which may be useful in monitoring the health of the patient may also be considered medical devices as used herein, such as but not limited to scales, pedometers, sleep trackers, accelerometers, motion sensors, and infrared (IR) sensors. Some of these devices 30 may be sent home with the patient 12 after a procedure, such as part of a post-operative kit, specifically contemplated for use with the digital coach 100. In other embodiments, the devices 30 may be obtained by the patient 12 at other times and may be operable independent of the digital coach 100. Each device 30 may include a transceiver that connects to the digital coach 100, either directly as seen in FIG. 1, or indirectly through the user's interactive device 13 as seen in FIG. 2. The connection to the digital coach 100 or interactive device 13 is preferably wireless, such as through a Wi-Fi network, Bluetooth® connection, or near-field connection such as facilitated by radiofrequency transmission. In other embodiments, however, the device(s) 30, 30', 30" may connect to the digital coach 100 through a wired connection, such as to the interactive device 13, through a USB or other similar connection.

Figure 3:
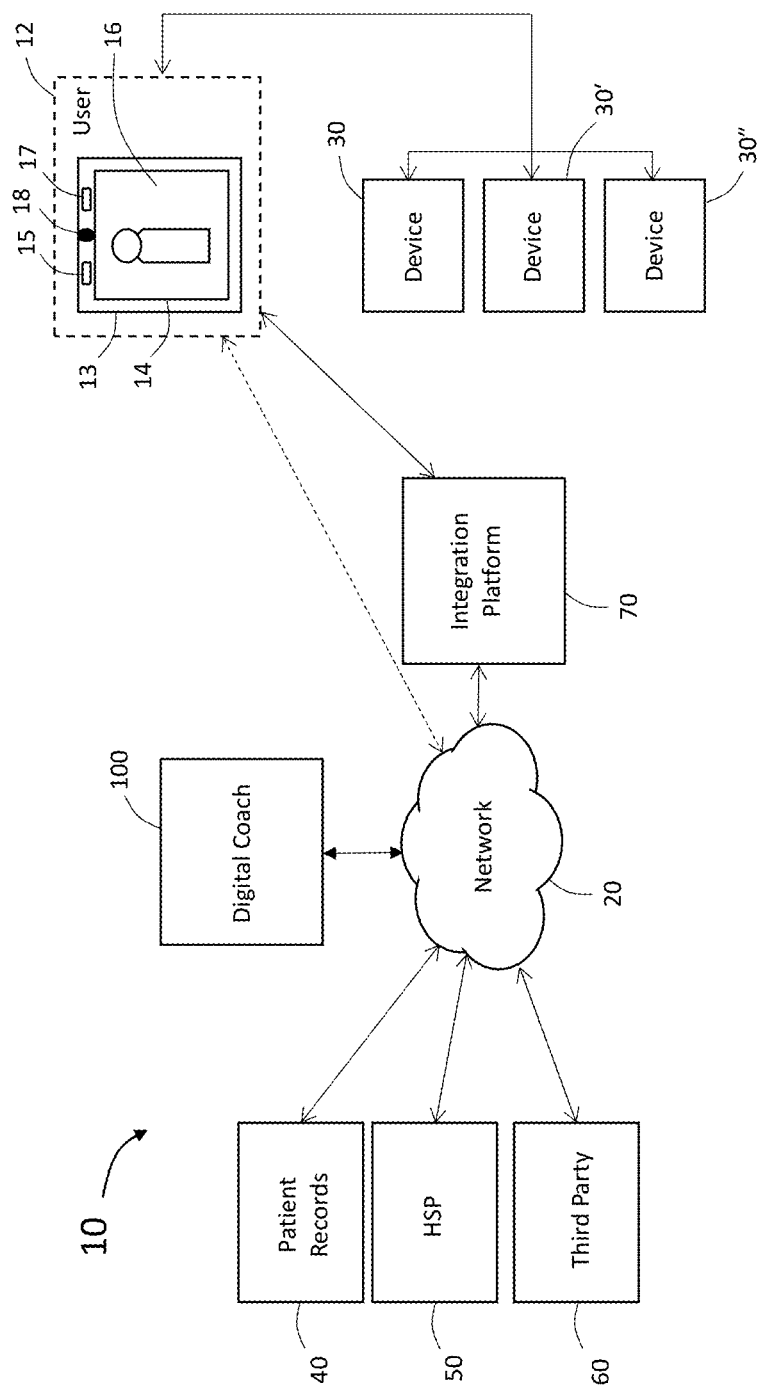
FIG. 3 is a schematic diagram of a third embodiment of the system.

In some embodiments, such as depicted in FIG. 3, an integration platform 70 may be interposed in electronic communication between the user's interactive device 13 and/or device(s) 30, 30', 30", and the digital coach 100. In such embodiments, the integration platform 70 may be used to covert the data from the device(s) 30, 30', 30" and the interactive device 13 into a format that can be interpreted by the processor 110 of the digital coach 100. For instance, the data can be converted into standard units recognized in the field for a particular type of data, such as beats per minute for pulse or systolic pressure over diastolic pressure for blood pressure. The integration platform 70 may also convert the data into digital or machine code, such as binary or hexadecimal. Systems such as those provided by Validic of Durham, N.C. may be used as an integration platform 70, for example, although other integration platforms 70 may also be used. It should further be appreciated that, in some embodiments, no integration platform 70 is needed.

Returning to FIG. 1, the digital coach 100 may also be in electronic communication with the patient's records 40, and may access the patient records 40 before, during or after a session with the user 12. The patient records 40 may include the patient's entire electronic health record (EHR), which are the digital files that make up a patient's medical and health history, and which may be updated by their various physicians or health providers during the course of treatment. For instance, the EHR may include biographical and background information about the patient; social and lifestyle information such as exercise, smoking, alcohol and drug use; family history of medical conditions; genetic predispositions to particular diseases or conditions; surgery history; medications being taken; allergies and contraindications for medications; past conditions; laboratory results; electronic medical records (EMR) from various physicians for their particular diagnoses and treatments, including SOAP notes from health providers; and other health, medical and medically-relevant information. In other embodiments, the patient records 40 may include only the EMR of a particular treating physician, such as the physician treating the patient for the particular condition that the digital coach 100 is being used to facilitate monitoring. In other embodiments, the patient records 40 includes only extracted files of the patient's complete health records, such as may be available on a patient portal for a particular treating physician or health service provider, or as may be available in a medical verification chip or other identifying device. Regardless of the format, these patient records 40 may be hosted remotely, such as in a cloud-based system, which may be the same or different than the location of the digital coach 100. Accordingly, the digital coach 100 may access the patient records 40 through the network 20 or Internet connection to read or download information from the patient records 40 for use locally within the processor 110 of the digital coach 100 and to update the patient records 40 with new information, as will be described in greater detail later.

The health service provider (HSP) 50 may also review and/or update information in the patient records 40, such as through an associated computing device that is in electronic communication with the network 20. The HSP 50 may be a treating physician, assisting physician, surgeon, physician's assistant, nurse practitioner, nurse, laboratory technician, pharmacist, physical therapist, trainer, dietician, psychiatrist, specialist, EMT, or other health or medical professional. Each patient may have any number of HSPs 50 that inform the patient records 40, and each can connect to, review and update the patient records 40, EHR or EMRs related thereto. In addition, the HSP 50 may provide specific information to the digital coach 100 that can be used in analyzing and interpreting the data, as will be described in greater detail. Finally, the HSP 50 may be contacted by the digital coach 100 during or after an interview with the user 12 to provide notifications, alerts, or updates on the patient's status to the HSP 50.

The processor 110 of the digital coach 100 may also be in electronic communication with and interface with a computing device associated with a third party 60. Third parties 60 may include, but are not limited to, laboratories performing lab tests, pharmacists, 911 or other emergency services, and emergency contacts. These third parties 60 may not be necessary in all circumstances, but in some instances, it may be beneficial for the digital coach 100 to be able to send them instructions or obtain information from them. For example, the digital coach 100 may be able to reorder prescriptions automatically for a user 12, query the status or results of a lab test for additional information to use in the analysis and interpretation of data, or automatically call 911 or order an ambulance if the user 12 is not responding or the data indicates the user 12 is experiencing tachycardia or is having difficulty breathing. The digital coach 100 may also send an alert to or notify the user's emergency contact, such as a relative or close friend, of the emergency situation so they can meet the user 12 at the hospital.

Figure 4:
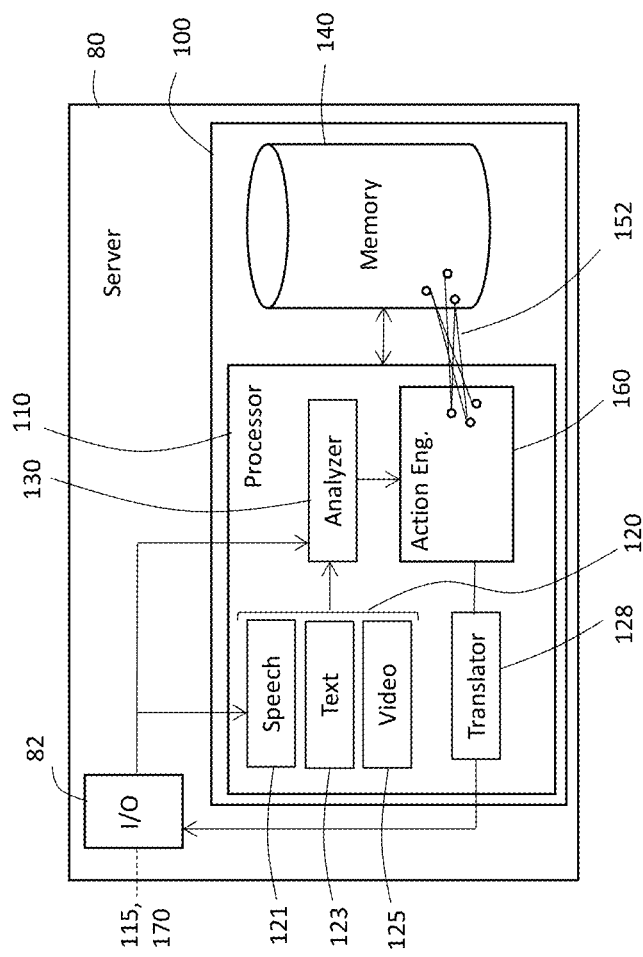
FIG. 4 is a schematic diagram of a server hosting the digital coach of the present invention.

As noted previously, the digital coach 100 may be hosted in a cloud-based system such as may be accessible through a connection to the network 20, such as the Internet. The digital coach 100 may be located on a server 80, and may further include a processor 110 and memory 140, as shown in FIG. 4. Either the server 80 or processor 110 may include an input/output (I/O) 82 for interfacing or communicating with the network 20 or other connection outside the server 80. For instance, data 115 may enter the digital coach 100 through the I/O 82 for analysis and interpretation. Instructions 170 determined by the digital coach 100 for the next action may be delivered to the network 20 for distribution to the user 12, devices 30, 30', 30", patient records 40, HSP 50 or third party 60 through the I/O 82. In some instances, the processor 110 may include one or more converter 120 for converting various types of data to digital signals or machine code for processing. For instance, a speech converter 121 may convert audio or sound, such as words spoken by the user 12 and captured by a microphone 17 or a wheezing sound captured by a stethoscope being used as a device 30. A text converter 123 may convert written text, such as typed responses from a user 12 and input into their interactive device 13 through a touch pad or keyboard. A video converter 125 may convert images of the user 12 captured by a camera 18 on the user's 12 interactive device 13, such as of the user 12 performing a certain task such as performing a range of motion test or cleaning a wound. These are a few non-limiting examples, and are intended for illustrative purposes. Any converters 120 capable of converting audio, video or text into digital data are contemplated and included here. Accordingly, converters 120 may be used within a processor 110 or on the server 80 in which the digital coach 100 resides, rather than using an integration platform 70 as described in FIG. 3.

With reference to FIGS. 3 and 4, the digital coach 100 includes memory 140 that includes a variety of modules 142, 142'. There may be any number of modules 142, such as from 1 to n number of modules 142". Each module 142 may be specific to a particular topic that may be presented to a user 12. For example, if the digital coach 100 is being used to monitor the patient following surgery, it may include modules 142, 142', 142" for wound healing, infection, and triage, respectively. There may be additional modules 142 for other conditions that do not relate directly to the primary purpose, but which nevertheless may impact the recovery process. For instance, modules 142 may be included for diabetes or Alzheimer's disease, if the patient is also diabetic (which can affect healing rates and recovery time) or Alzheimer's (which may make affect the patient's memory, impair accurate patient response or remembering aspects of the post-operative procedures that could negatively affect following protocol). Health or lifestyle modules 142 may also be included, such as if the patient is a smoker or an athlete. For instance, these modules may address that smoking should be ceased or decreased during recovery, or that physical activity can resume after 2 weeks but training should wait for 6 weeks to resume, for example.

Figure 6:
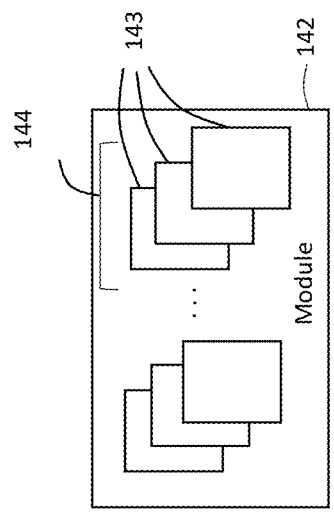
FIG. 6 is a schematic diagram of an illustrative module of the digital coach.

As shown in FIG. 6, each module 142 includes various series 144 of scripts 143. The scripts 143 are pre-recorded information, such as audio and/or video of a person speaking to provide information to the user 12. For example, in at least one embodiment the scripts 143 may present to the user 12 on the display of their interactive device 13 as a video of a person speaking the attending lines, and possibly demonstrating a technique. In other embodiments, the scripts 143 may present to the user 12 as a voice, similar to Amazon's Alexa. The scripts 143 may present to the user 12 in the user's preferred language, including American Sign Language (ASL).

Accordingly, as used herein, "audio" includes a video of sign language, and refers to verbal data. The scripts 143 may be translated into any language, such as with a translator 128 shown in FIG. 4, prior to being presented to the user 12. A single script 143 may be a single sentence, such as "Now let's take your blood pressure." In other embodiments, a single script 143 may be a group of sentences that convey information, such as "It seems that the needle did not penetrate the skin. Please reposition the needle and try again." In other embodiments, a single script 143 may be an entire dialogue or presentation, providing a demonstration or additional information to the user 12, such as going over pre-operative procedures or demonstrating how to clean a wound thoroughly or change bandages.

The scripts 143 may be grouped into series 144, which are sub-sets of the module 142. For instance, a module 142 on wound care may include a series 144 on wound cleaning, another series 144' on healthy and non-healthy wound appearance, and so forth. The various scripts 143 within a series 144 will all relate to that sub-topic, such as wound cleaning. Some of the series 144 or scripts 143 may be cross-referenced within the memory 140 between different modules 142 if they apply to multiple different modules. For example, a script 143 of "The yellow fluid around the stitches is pus, and indicates you could have an infection" may be present in both the module 142 for wound care and another module 142' for infections. Such cross-referenced scripts 143 may be located in one location on the memory 140 and other modules 142 may map to that location as needed. In other embodiments, each module 142 may include all the necessary or possible scripts 143 that are relevant to that module 142. The digital coach 100 may include as many modules 142 as apply to a particular user 12, their health or medical history, and the condition(s) or treatment(s) for which digital coach 100 is being used to monitor and assess. Accordingly, each module 142 may include as many scripts 143 and series 144 as may be necessary to complete the given module 142, and preferably cover as many possible outcomes, scenarios and information as can be contemplated.

In some embodiments, the scripts 143 within a series 144 or module 142 may be initially set for presentation to the user 12 in a pre-established order. For example, scripts 143 within a series 144 on triage may present questions to the user 12 of a type and in the order validated for triage scale, such as the Emergency Severity Index (ESI). In such embodiments, script(s) 143 are presented to the user 12 in a preselected order to obtain the most important, time-sensitive, or highest priority information first, with lower priority information being obtained later. In the case of triage, for example, it is of higher priority to determine if the user 12 is having difficulty breathing or is experiencing an irregular heart rate than if the user 12 has a fever or is experiencing abdominal pain. In some embodiments, however, the order of the script 143 presentation is loosely established and the digital coach 100 is more flexible in determining the order of presentation. This order of presentation of scripts 143 may still be preselected, but may be more variable in execution based on the responses from the user 12 and the data from the devices 30.

Figure 5:
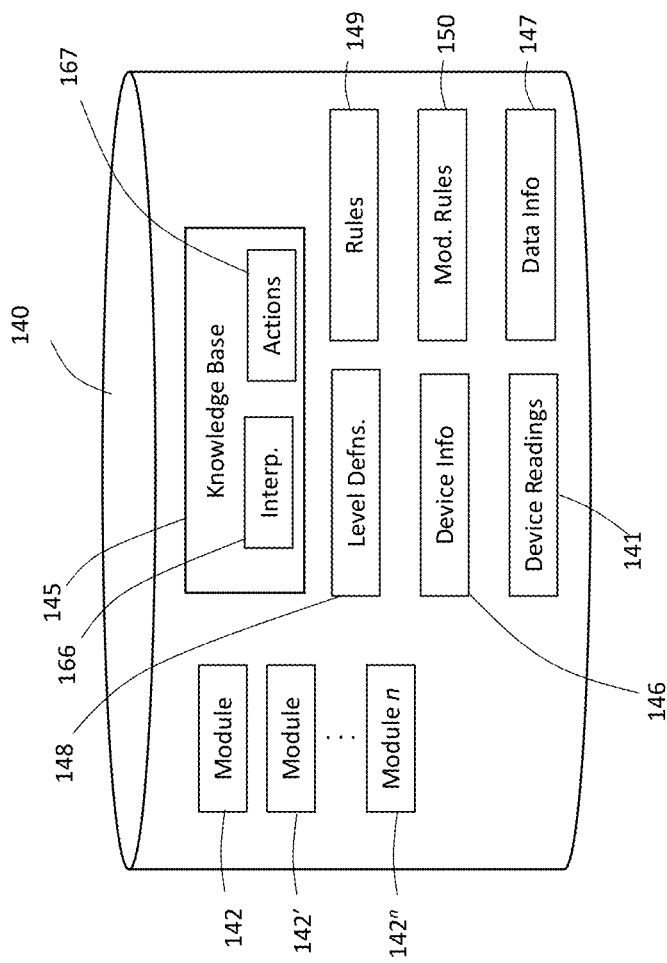
FIG. 5 is a schematic diagram of one embodiment of the memory of the digital coach of the system.

Returning to FIG. 5, the memory 140 also includes at least one knowledge base 145 that includes known information and correlations between information for various fields. These knowledge bases 145 are prepopulated and informed by experts in each field, and may include definitions, content from textbooks, treatises, journals, encyclopedias, and other information relative to various topics. The knowledge base 145 may also include questions and various answers that may be responsive to the questions, providing an initial database of information, which can be adaptively expanded through use of the digital coach 100. In at least one embodiment, each module 142 corresponds to a dedicated knowledge base 145 which includes facts and knowledge relevant to the topic of that particular module 142. In other embodiments, a knowledge base 145 may include information corresponding to multiple modules 142, and may be cross-referenced or mapped by various different modules 142.

The knowledge base 145 specifically includes various predefined interpretations 166 that are each comprised of first data 116 that is verbal in nature, second data 118 that is numerical in nature, and semantic information 162 that correlates to the first data 116 and second data 118. These predefined interpretations 166 define correlations and/or interpolations between data and known information in the various relevant areas, and can be used to connect information and data and draw inferences about data received from the user 12 or device(s) 30 during a session or interaction.

The knowledge base 145 also includes a series of actions 167 corresponding to each of the predefined interpretations 166. For example, a predefined interpretation of "less than 12 years old" and "temperature of 102.6" corresponds with at least one action, such as "administer child-appropriate fever-reducing medication" and "apply cool compress to forehead."

The memory 140 may also house specified databases, such as a device information database 146, data information database 147, and device readings 141. The device information database 146 includes information on various types of devices 30 that may communicate with the digital coach 100. For example, the device information database 146 may be populated with the type, make, model, manufacturer, and serial number of each of the devices 30 that may be utilized in the system 10, as well as the type of data and units of measurement in which the data is reported for each specific device 30. This information allows the digital coach 100 to recognize the incoming data 115 from the various devices 30 and know how to interpret the data. A data information database 147 may also be included, which keys the information according to data type. For instance, the data information database 147 may include lists of the various types, makes and models of devices that produce a particular type of data, and the units in which they report the data. In some instances, the data information database 147 may be cross-referenced to the device information database 146. A device readings database 141 may be included to store data from the devices 30, 30', 30" from previous sessions for comparison during the current session. For instance, the device readings from a blood pressure cuff taken during each session can be stored, and may form a piece of semantic information 162 with respect to a subsequent session. Statistical assessments of the various readings can also be stored in the device readings 141, such as the average blood pressure measured over the last month, or the highest blood pressure measured in the last week. The measurements in the device readings database 141 may be identified, sorted and/or stored according to type of data measurement or device from which the measurement derived. Each of the device information database 146, data information database 147, and device readings 141 may be specialized subsets of knowledge bases 145, or may be parsed as separate databases.

The memory 140 also includes level definitions 148 which are used to analyze incoming data. The level definitions 148 define various levels of assessment or risk, and may collectively define an escalating scale of concern. Each module 142 or topic may have dedicated level definitions 148 that are specific to a particular condition or treatment being monitored. For example, level definitions 148 for diabetes may include target or normal, low, dangerously low, high, and dangerously high levels or ranges. As used herein, the terms "level," "range," and "category" may be used interchangeably. The levels may be defined by reference points that indicate the boundaries or limits of each level, and may be specific to a type of data, such as fasting versus non-fasting values. For example, reference points of 71-110 mg/dL may define a target or normal fasting blood glucose level; 51-70 mg/dL defines the low range; 50 mg/dL defines the upper limit of the extremely low range; 111-200 mg/dL defines a medium range; 201-280 mg/dL defines the high range, and 281 mg/dL indicates the lower limit of the extremely high range. This is but one illustrative example and is not intended to be limiting. In some embodiments, the levels definitions 148 may include only two levels, such as acceptable and not acceptable. In other embodiments, the level definitions 148 may include as many levels and sublevels as may be necessary for the given condition being monitored.

The memory 140 further includes at least one bank of rules 149. The rules 149 provide instructions for operations to the data 115 to be used in analyzing and/or interpreting the data 115. For example, the rules 149 may include "if, then" instructions based on the level or range where the data falls and some action(s) that is suggested to be taken as a result. These rules 149 are predetermined based on recognized medical diagnoses and protocols that are also pre-populated in the rules 149 bank of the memory 140. For instance, one example is "if the heart rate is in the high range, then perform at least one of the following: check for activity level and time since activity; check perspiration levels; check breathing rate; notify third party." In a preferred embodiment, at least one rule requires the digital coach 100 to notify a third party or provide an alert to an HSP or emergency contact for any data that falls into the extremely high category. In at least one embodiment, a rule may exist to notify the HSP for any data that falls into a high category. In at least one embodiment, there may be a bank of rules 149 corresponding to each module 142, knowledge base 145, and/or level definitions 148. In other embodiments, there may be banks of rules 149 corresponding to topics, and the rules 149 are applied to each module 142, knowledge base 145 and/or level definition 148 as necessary.

At least one bank of modification rules 150 may also be included. The modification rules 150 may be applied to the rules 149 and level definitions 148 to deviate from the standard according to preselected parameters. For example, the modification rules 150 may include modifiers to level definitions 148 for mean blood glucose levels at different altitudes above sea level. Application of these modification rules 150 to the level definitions 148 adjust the reference points defining each level up or down accordingly. As another example, a patient's medical history, such as may be accessed from their patient records 40, may be applied as modification rules 150 to modify rules 149 or level definitions 148 specific to a particular patient. For example, the reference points for blood pressure defining high, low, and normal blood pressure ranges may be modified depending on the age of the patient. High blood pressure may be defined between 130/86-144/90 mm Hg for a man who is 55 years old, whereas it may be defined between 123/82-135/86 mm Hg for a man who is 35 years old. Similarly, a modification rule 150 may be applied to level definitions 148 for a person who has been diagnosed as having high blood pressure, so that the "normal" level is redefined to accommodate the higher blood pressure levels.

Figure 7:
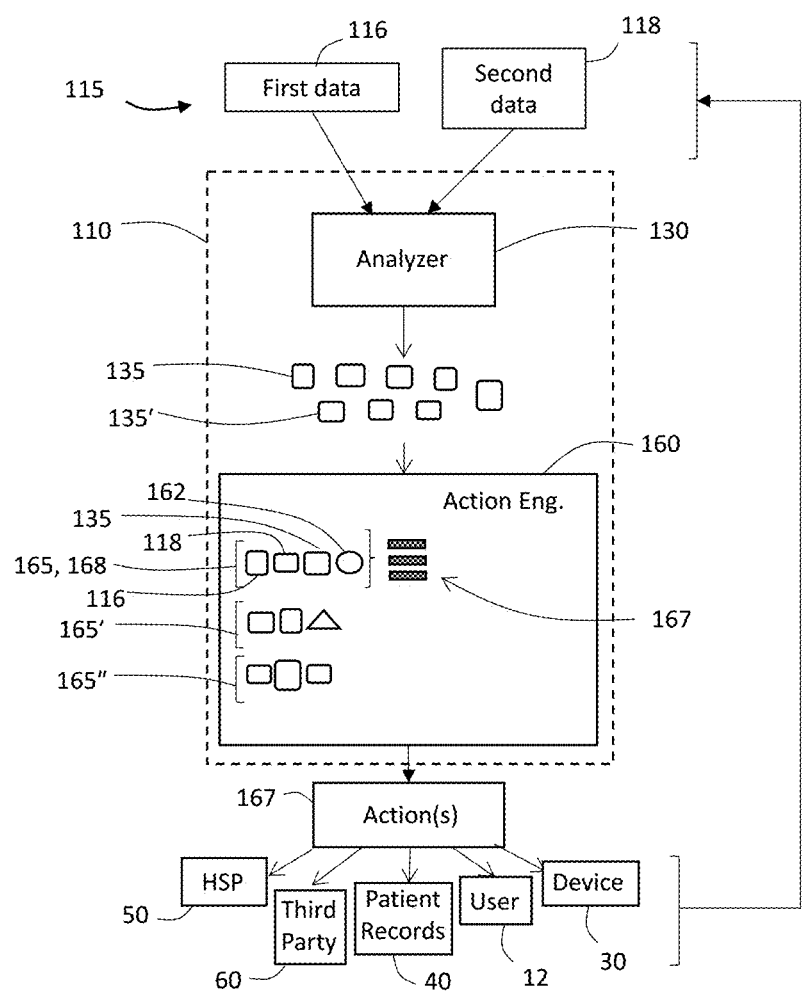
FIG. 7 is a schematic diagram of the digital coach and the various components of the processor that perform the analysis and interpretation of the data.
Figure 8:
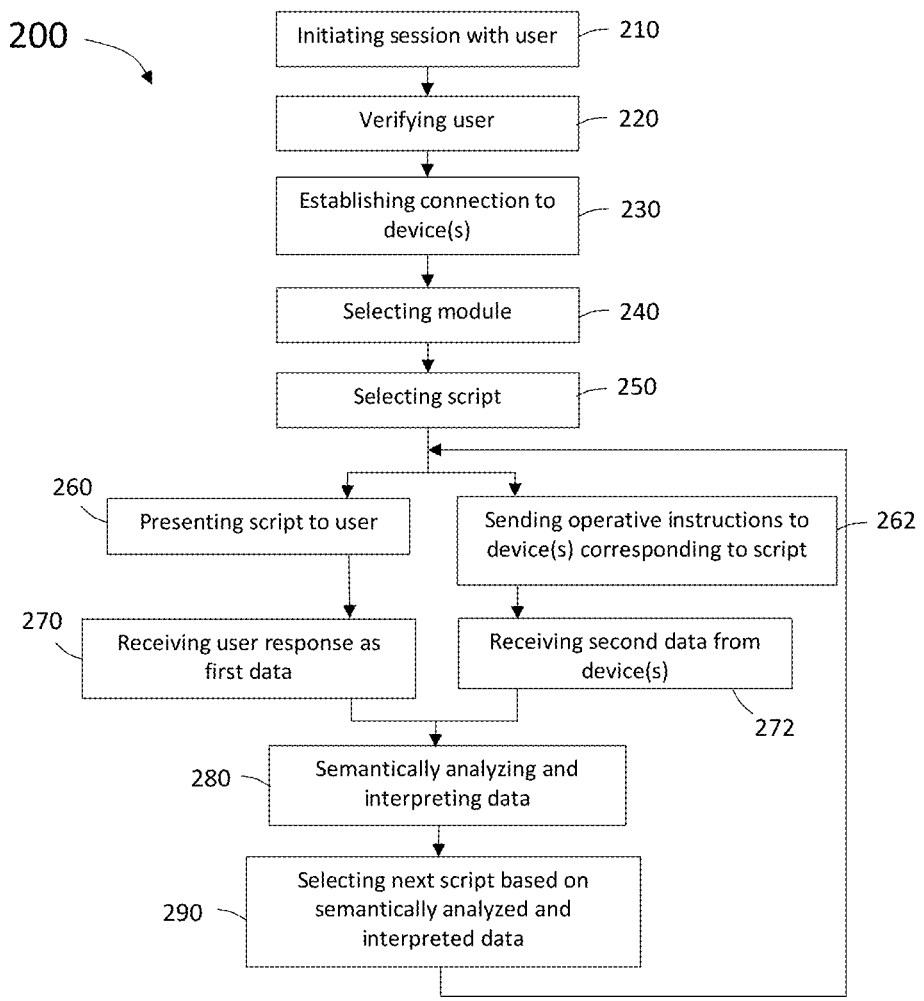
FIG. 8 is a schematic diagram of a method of conducting a session between the digital coach, a user, and at least one device.

Referring to FIGS. 4 and 7, the processor 110 of the digital coach 100 also includes an analyzer 130 that takes incoming data 115 and analyzes it. In one embodiment, the analyzer transforms the data 115 into assessments 135 for subsequent interpretation. The incoming data 115 may be first data 116 corresponding to user-provided responses, which can be at least one of spoken words, written text and motion by the user 12 in response to a question from the digital coach 100, such as "I'm feeling terrible today" in response to the question "How are you feeling?" The incoming data 115 may also be second data 118 from a device(s) 30 and which are indicative of at least one physiological condition of the user 12. The second data 118 can come to the processor 110 directly from the devices(s) 30 or indirectly through the user's interactive device 13. The second data 118 may be qualitative, such as a reading of "good" from a medical device 30, or quantitative, such as the numerical pulse reading delivered from a pulse oximeter. The first and second data 116, 118 may be converted by an integration platform 70, or a converter 120 within the server 80 or processor 110 of the digital coach 100, before entering the analyzer 130. In other embodiments, the data 115 are not converted and enter the analyzer 130 in the same format in which they were generated.

In at least one embodiment, the analyzer 130 receives each piece of data 115, identifies the type of data, and compares it to the relevant level definitions 148 to assign the data 115 to an appropriate category. As an illustrative example, the analyzer 130 identifies data of "120/80" as blood pressure data, compares it to the level definitions 148 for blood pressure, and determines the data is in the "normal" range. The analyzer 130 combines or associates the "normal range" with the "120/80" data to form an assessment 135 of the data. The assessments 135 may be considered an analysis of the data 115 as compared to known standards or modified levels specific to a patient. These assessments 135 may then combined and semantically expanded in the action engine 160 of the processor 110 to form candidate interpretations 165 of the data, such as with reverse indexing or other suitable method.

In at least one embodiment, the data 115 enter the action engine 160 directly, without being first categorized by the analyzer 130. The action engine 160 compares the first and second data 116, 118 to the first data, second data, and semantic information components of the predefined interpretations 166 stored in the knowledge base 145 to form a series of candidate interpretations 165. In some embodiments, the assessments 135 are also included and compared to the information provided in the predefined interpretations 166. These candidate interpretations 165 represent various different interpretations of the first and second data 116, 118 based on correlations and interpolations between the data and information that is known in the medical and health fields. These correlations or interpretations indicate a relationship between information that could go together. For example, an assessment of "high blood pressure" may be combined with the semantic information "there is a high correlation of people with COPD and people with high blood pressure." The quantitative measurement of blood pressure may be added to this string of information, as well as a modifier that this particular patient has COPD, to form an interpretation 162 that the high blood pressure numbers being reported for this patient is high by typical standards, but is normal for this patient and is normal for COPD patients. The semantic information 162, 162' may be related to one or many assessments 135, 135' to form an interpretation 165. Some interpretations 165' may not include any semantic information 162 or any assessments 135.

The candidate interpretations 165 are prioritized based on a degree of similarity to the predefined interpretations 166 stored in the knowledge base 145. A primary interpretation 168 is selected from the list of candidate interpretations 165. In at least one embodiment, the primary interpretation 168 is the candidate interpretation 165 that has the highest degree of similarity to a predefined interpretation 166 stored in the knowledge database 145.

The action engine 160 of the processor 110 then generates at least one action 167 based on the primary interpretation 168. Since each predefined interpretation 166 has at least one action associated therewith, the at least one action 167 generated for the primary interpretation 168 is the at least one action associated with the matching predefined interpretation 166 stored in the knowledge base 145. The processor 110 then executes the at least one action corresponding to the primary interpretation 168. For example, the action may be to instruct the interactive device 13 to present a subsequent script 143 to the user 12, which may say "You're right on track. I'll check back in with you tomorrow." Which script 143 will be selected for presentation as the next subsequent script will depend on the first and second data 116, 118 and the interpretation thereof as the primary interpretation 168. In a preferred embodiment, the processor 110 selects the subsequent script 143 based on the primary interpretation 168.

In other embodiments, the action engine 160 of the processor 110 may apply at least one rule 149 to the candidate interpretations 165 to generate at least one action 167 to take. The same rule 149 may be applied to all the candidate interpretations 165, or various rules 149 may be applied to various candidate interpretations 165 depending on the first and second data 116, 118, assessments 135, and semantic information 162 contained therein. Further, these rules 149 may be standard rules, or may be modified according to modification rules 150, such as to adjust the parameters to take into account a patient's medical history for example. The rule 149 being applied may be different depending on how many assessments 135 and pieces of semantic information 162 are related to one another. For instance, an interpretation 165 that includes "temperature of 103.6 degrees Fahrenheit" and "four years old" could result in an action of "administer child-safe medication to reduce fever" as an action. However, an interpretation 165 including "temperature of 103.6 degrees Fahrenheit," "four years old," "medication administered 1 hour ago," and "children's Tylenol," could result in an action of "go to an urgent care center immediately." The additional information could result in a different interpretation 165 that changes the resulting action item. In the above example, a child having a fever indicates medication should be given to reduce the fever. Knowing the child already received fever-reducing medication an hour ago indicates the medicine is not working to reduce the fever, and the situation could be fatal and should receive immediate attention. This is just one illustrative example, and is not intended to be limiting in any way.

The rules 149 may have an "if, then" format, where the first data 116, second data 118, various assessments 135 and pieces of semantic information 162 are conditions precedent to some action 167. The action 167 may follow if all the conditions precedent (the first data 116, second data 118, various assessments 135 and pieces of semantic information 162 in a candidate interpretation 165) are present or true. In other instances, the action 167 may follow if a certain percentage of the conditions precedent are present or true, such as 70% or 90%. In some instances, different actions 167, 167' may be the result of application of a rule 149 where only certain conditions precedent are present, such as action A results if only 70% of the conditions precedent are met, whereas action B results if 80% are met, and action C results if 90% are met. The resulting actions 167 may also differ depending on whether certain specific first data 116, second data 118, assessments 135 or pieces of semantic information 162 are present in a candidate interpretation 165. For instance, action A may only result when both "high blood pressure" and "COPD" are present together in an interpretation 165. Accordingly, multiple rules 149 may be applied to the same candidate interpretation 165, and multiple actions 167 may result from rules 149 applied to the same candidate interpretation 165.

In still other embodiments, rules 149 may not be applied to the candidate interpretations 165. Rather, the candidate interpretations 165 are subjected to a machine learning system 152, schematically depicted in FIG. 4. Examples of a machine learning system 152 include, but are not limited to, neural networks and hybrid systems. The machine learning systems 152 may begin with a few thousand rules, and soft matching occurs initially to train the system. As the system 152 is used, it increases its accuracy in soft matching. It may employ probabilities or weighting to provide a statistical analysis of the probability or likelihood that the first data 116, second data 118, assessments 135, and semantic information 162 in a candidate interpretation 165 correspond to a particular action 167. For example, certain words or phrases may not directly match with the expected words or data in a rule that would signify a particular predefined interpretation 166, but over time, pathways leading to that particular predefined interpretation 166 become stronger through greater use, and the machine learning system 152 weights those enhanced pathways greater than other, less used pathways. Over time, certain combinations of first data 116, second data 118, assessments 135, and semantic information 162 may become recognized as particularly significant to indicate a particular predefined interpretation 166. The significance may be a statistically significant level, such as a 95% confidence or significant as measured by some other statistical method. These are just a few examples, and are not meant to be limiting.

In other examples, the machine learning system 152 applies weights, such as a numerical modifier, to candidate interpretations 165, sub-units or combinations of first data 116, second data 118, assessments 135, and semantic information 162. This weighting may be inverse document frequency based, and indicates a level of importance of the attached interpretation 165, sub-unit or combination of assessments 135 and semantic information 162 to particular actions 167.

The possible actions 167 may be pre-populated in a database in the memory 140, such as in the knowledge database 145, and are accessed by the action engine 160 of the processor 110 in generating a list of possible relevant actions 167 for the various candidate interpretations 165 present for the given data 115. To generate actions 167, the action engine 160 of the processor 110 may apply the rules 149 to the interpretations 165, access the database of actions 167 in the memory 140, and determine which actions 167 are most likely relevant, significant, or are the highest match to the interpretations 165. This may be accomplished by application of an algorithm, equation, calculation or other suitable method. A list of possible relevant actions 167 may therefore be generated, as depicted in FIG. 7. The actions 167 may be sorted, such as according to priority, urgency, or most likely fit the scenario. This may be accomplished in a number of ways. For example, if one of the interpretations 165 indicates an emergency situation, the corresponding action 167 may be given the highest priority to ensure the emergency is addressed first. In this manner, a high heart rate indicating tachycardia is given higher priority than an alarm indicating it is a prescheduled time to check the status of stitches. The resulting action of "call 911 for an ambulance" takes precedence over the other resulting action of checking the stitches.

The processor 110 of the digital coach 100 will select one of the generated actions 167 to follow. In at least one embodiment, the action 167 with the highest priority is selected. In other embodiments, however, the action 167 that has the greatest weight, is the most statistically probably, or has appeared the most frequently in the action engine 160 may be selected. There may be rules 149 that drive how the digital coach 100 chooses which action 167 to follow. There may also be exceptions that override the rules 149, such as when an emergency situation is indicated.

When the processor 110 of the digital coach 100 chooses an action 167 to follow, it executes the action 167 and communicates with an appropriate entity. Executed actions 167 may take different forms depending on the intended recipient 180. For instance, as shown in FIG. 7, an executed action 167 for further information from a user 12 may include identifying the script 143 corresponding to the selected action 167 and presenting the script 143 to the user 12. For instance, the action 167 may be "obtain information on activity level." The corresponding script 143 may be a video of an avatar saying "It seems your heart rate is elevated. Have you been moving around or exercising recently?" As noted previously, the script 143 may be translated into the user's preferred language by a translator 128 prior to being presented to the user 12. An executed action 167 to seek to obtain data from a device 30 may include sending operative instructions to the device 30 to activate, calibrate the device, initiate data collection, and/or transmit data to the digital coach 100 for processing. An executed action 167 may also be directed to the patient records 40, which may include updating the patient records 40 to include the recently acquired data 115 and the analysis and interpretation that resulted from that data. In some embodiments, an executed action 167 may also be directed to the HSP 70, such as to provide an alert to the HSP 50 of a condition that has arisen with the patient which needs medical attention or follow-up, or to request a prescription renewal for instance. An executed action 167 may also be directed to a third party 60, such as a pharmacy to check the status of a prescription. These are just a few illustrative examples, and are not intended to be exhaustive or limiting.

Executed action 167 may be directed to as many of the recipients 180 as necessary to complete the chosen action 167. For instance, a script 143 may be presented to a user 12 and operative instructions may be simultaneously sent to a device 30 to collect further information and data from the user 12 and device 30. An alert may be sent to the HSP 50 and an emergency service as third party 60 in the event of an emergency, such as "the patient is on a morphine pump, which has been initiated 5 times in the last hour. The patient reports they are feeling no pain. When asked to count backwards from 100, they patient was only able to reach 98. Here is a video of the patient performing this task . . . " Simultaneously, a script 143 may also be presented to the user 12 that says "An ambulance has been called for you. Please stay calm and know that help is on the way." The digital coach 100 may also coordinate a three-way session between the user 12 and the third party 60, such as an EMT who is on the way to the patient, to begin providing visual and auditory information to the EMT. For instance, the digital coach 100 may coordinate the collection of video and audio data of the patient and transmit or stream these data to the EMT so they can see if the patient is breathing and can tell them things they can do to be more calm or comfortable until the ambulance arrives.

As additional data 115 is received by the digital coach 100, the processor 110 analyzes and interpret the new data 115 as previously above. Accordingly, the digital coach 100 may involve an iterative process or feedback loop that analyzes and interprets data step-by-step, to determine which action is most appropriate at each step. Therefore, while the modules 142, scripts 143, knowledge base(s) 145, predefined interpretations 166, and associated actions 167 may be pre-established and stored in memory 140, they are dynamically selected and presented based on up-to-date information. The sessions between the digital coach 100 and the user 12 may therefore take any path, to be determined adaptively as the session progresses. It is not pre-set and does not follow a particular path. Nor does it follow a pre-established decision tree of yes-no pathways. Rather, the session is dynamic and adaptive to the user 12, the devices 30, and the data 115 collected from them of a patient's health or medical condition at a given time. Likewise, the processor 110 of the digital coach 100 does not use look-up tables, but rather semantically analyzes data 115 to determine, at that moment, what the best course of action is. As used herein, "semantic" as applied to analysis of data includes analysis of both words and numerical data, and indicates a correlative relationship between data and pieces of information. The processor 110 is not merely analyzing data according to rules, but is semantically expanding and analyzing it to identify correlations based on known and suspected connections and relationships between words, phrases, and quantitative data to arrive at a series of possible interpretations and actions that it ranks to determine the best likely course of action. In some embodiments, the digital coach 100 may even learn over time and improve its accuracy.

In practice, the digital coach 100 may perform a method of conducting an automated interview with a user and an associated device, as at 200 in FIG. 7. The method 200 may begin with initiating a session with a user, as at 210. A "session" with the user may be defined as the presentation of scripts 143, collection of responses from the user 12 and/or data from devices 30, and further presentation of scripts 143 in response to the user input and collected data based on analysis and interpretation of the user input and collected data. In at least one embodiment, the digital coach 100 initiates the sessions. Initiating a session, as at 210, may include establishing a connection to the user's interactive device 13 through the network 20 or Internet, such as by activating the interactive device 13 and opening a corresponding local program for interaction through the session. Initiation may occur according to a preselected schedule that is tailored to the user 12 by the HSP 50 according to a treatment plan or post-treatment procedures. For instance, the digital coach 100 may include instructions to initiate a first session with the user 12 at 24 hours following release of the user 12 from the medical facility, although shorter or longer time periods may also be used for an initial session. Additional sessions may be scheduled for subsequent times during the monitoring period in which the digital coach 100 will be used, such as days and weeks after the initial session if the expected recovery or post-treatment health of the user 12 is normal or as expected. The schedule of sessions may be altered by the digital coach 100 if abnormal events or emergency situations arise during the session, as determined by the digital coach 100 from the analysis and interpretation of data 115 obtained during the sessions. In other embodiments, the user 12 may initiate a session, such as to remind themselves of a particular point that was covered previously, to get information about the status of their progress or to confirm a follow-up appointment, or to obtain advice on an unexpected medical situation that has arisen such as a fever, redness or swelling that has occurred between scheduled sessions.

In some embodiments, the method 200 may include verifying a user, as at 220, at the beginning of a session to make sure the appropriate person is being addressed. Verification may also be useful to ensure patient privacy and adhere to HIPAA requirements for the treatment of medically-sensitive information. Verification may be accomplished by verification systems, such as requesting and obtaining a user's login and password, or by obtaining biometrically identifying information of the user such as fingerprint, retinal scan or facial recognition using the interactive device 13. In some embodiments, user verification may be accomplished by confirming a serial code with a peripheral device such as a Fitbit, medical alert bracelets or other accessories that may include an RFID tag or other readable medium to identify the wearer. In some embodiments, these tags may also be linked to the person's patient records 40 to verify the wearer.

The method 200 also includes establishing a connection to the device(s), as at 230. Any peripheral or medical device may be connected to the digital coach 100 to receive instructions and transmit data. In some embodiments, the devices 30 may connect to the digital coach 100 through the network 20, which may be further facilitated by Wi-Fi, Bluetooth®, near-field, or other similar wireless connection to or through the user's interactive device 13. In other embodiments, the devices 30 may have a sensor(s) and/or transceiver to directly receive instructions from and transmit data to the digital coach 100 without the use of the user's interactive device 13. Any combination of direct connection or connection through the user's interactive device 13 is contemplated among the various devices 30. In addition, the digital coach 100 may establish a connection to other peripheral devices that do not collect or provide data, but nevertheless may be operated remotely by the digital coach 100. For example, the patient may use a medical bed at home, and the bed may have various sensors and actuators to adjust the height and angle of inclination of various parts of the bed, such as the head, foot or torso sections of the bed. The digital coach 100 may send operative instructions to the bed to adjust the inclination, such as if the patient says they are uncomfortable during a session. The digital coach 100 may then ask the patient a follow-up question after adjusting the bed to see if the new position is better or worse, or which part of the bed they want adjusted and in what direction.

The method 200 may include conducting a session, which begins with selecting a module, as at 240 and selecting a script, as at 250. The initial module and script may be pre-established according to the rules, which may follow a post-treatment protocol established by the treating physician or HSP 50. In at least one embodiment, the initial module and script may be a greeting and introduction, with an explanation to the user of the purpose of the digital coach 100 and how to use it. In other embodiments, the initial module and script may be geared toward a particular topic for data collection, such as blood pressure, heart rate, and breathing for general health. Any module 142 or script 143 may be selected, and may be chosen according to a pre-established schedule or other information.

Once the processor 110 of the digital coach 100 selects a module and script, the method 200 continues with presenting the script to the user, as at 260. As described previously, presenting a script to a user preferably includes the processor 110 of the digital coach 100 directing the interactive device 13 to the selected script 143 located in the memory 140 and instructing the interactive device 13 to play the video (or a translation thereof) on its display 14, such as a monitor or screen. Speakers 15 provide the accompanying audio. In other embodiments, the processor 110 transmits the script 143 to the user's interactive device 13 with instructions to play the script 143 on the interactive device 13. The script 143 may be presented to the user 12 in any appropriate format, which may be any combination of visual, auditory, and textual presentation, and may use any suitable program to accomplish this task.

The method 200 may also include sending one or more operative instructions to a device(s), as at 262. The processor 110 of the digital coach 100 also sends these operative instructions. The operative instructions may correspond to the script 143 being presented to the user 12, and may be coordinated to operate the device 30 and collect data simultaneously with the presentation of the script 143 to the user 12. For example, the script 143 may say "Let's take your blood pressure. Please place the blood pressure cuff on your arm as shown here, and say 'OK' when you have it in place" then wait for the user to say OK, then proceed with "Alright, I'm going to inflate the blood pressure cuff and take a reading. Please hold still while I do this." Operative instructions may be sent to the blood pressure cuff as this last clip is played, and the cuff will receive the instructions and begin to inflate. This is just one example for illustrative purposes.

The method 200 further includes receiving user response as first data, as at 270. As noted above, during each session, the digital coach 100 presents scripts 143 to the user 12 in a step-wise manner to obtain data 115 and assess the user's health and/or medical status. When the script 143 is finished, the digital coach 100 may enter a listening mode in which it waits for a response from the user 12. For example, the processor 110 of the digital coach 100 in the listening mode may simply monitor for a response to be received. In other examples, the processor 110 of the digital coach 100 may send operative signals to the interactive device 13 to record a video and/or audio of the user 12 during listening mode, which will then be transmitted to and received by the processor 110 of the digital coach 100 for processing. The processor 110 may also include facial recognition capabilities to interpret emotions and non-verbal information from a video of the user 12, such as body language and pupil dilation. This can be helpful, for instance, in determining if the user 12 is anxious, which can affect recovery time, or is accurately self-reporting on their status, which can affect the analysis and interpretation of the remaining data. As used herein, "recording" may encompass both inscribing the user's response in memory for storage, as well as transient collection of the user's response for transmission, where the response may be stored only in a temporary cache and not in long-term memory. The user's response is transmitted to the processor 110 of the digital coach 100 and is input as first data 116.

The method 200 similarly includes receiving second data from device(s), as at 272. These data may include quantitative or qualitative data, as previously described. The device(s) 30 may transmit the second data 118 once it is all collected, or may stream the second 118 data as it is being collected, and may be routed through the interactive device 13 as a communications controller or device manager in some embodiments. In some embodiments, the processor 110 of the digital coach 100 may retrieve the second data 118 from the device(s) 30 if the devices are passive and only collect data.

Figure 9A:
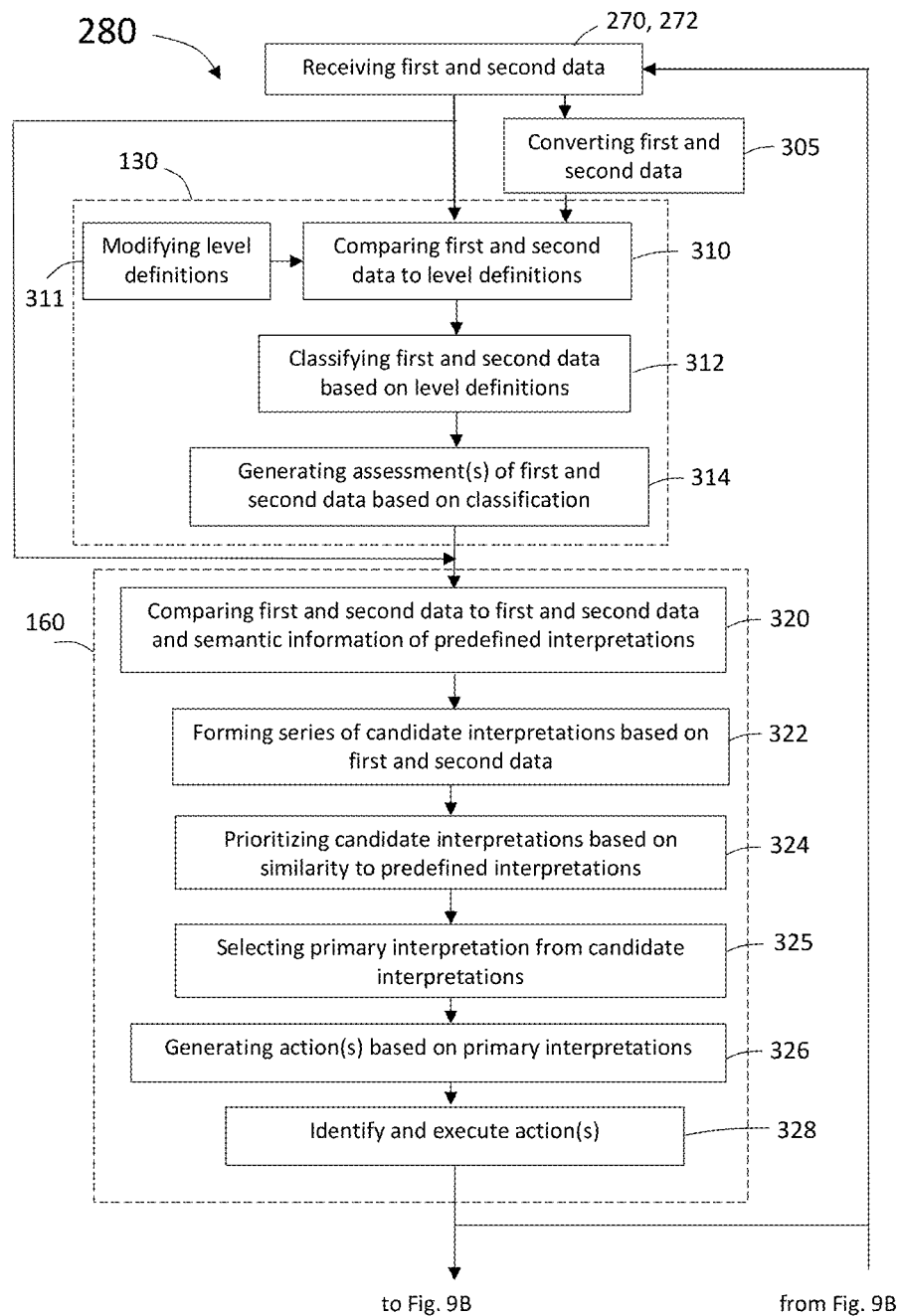
FIG. 9A is a first portion of a schematic diagram further illustrating the step of semantically analyzing and interpreting data as shown in FIG. 8, with the rest of the diagram continued in FIG. 9B.
Figure 9B:
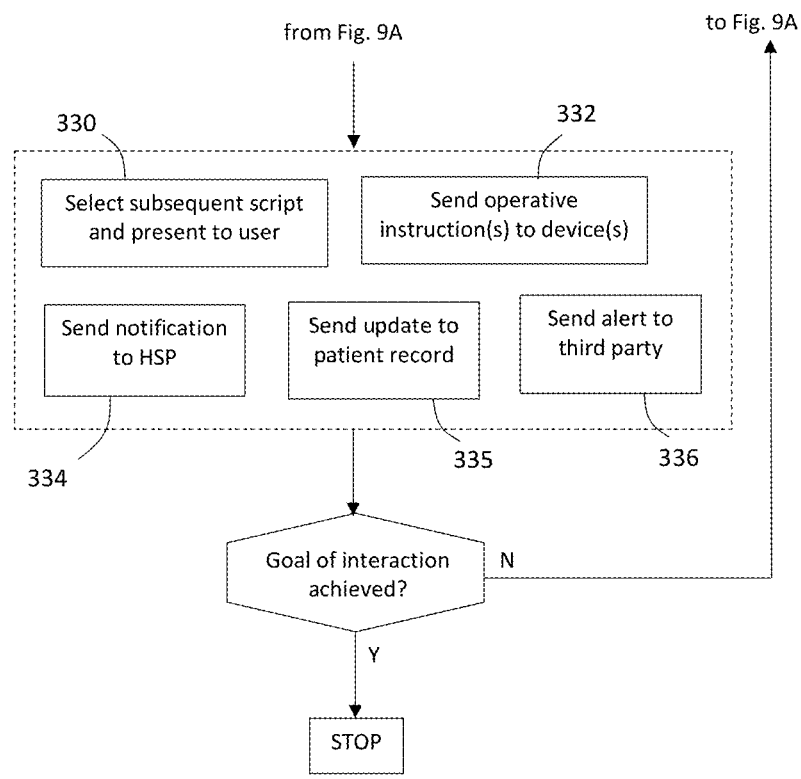
FIG. 9B is a second portion of the schematic diagram illustrating the step of semantically analyzing and interpreting data as shown in FIG. 8, which continues from the first portion shown in FIG. 9A.

The method 200 continues with semantically analyzing and interpreting the first and second data, as at 280. Referring now to FIGS. 9a, 9b, and 4, the step of semantically analyzing and interpreting the data occurs within the processor 110 of the digital coach 100, and may include converting the first and second data, as at 305. Converting the first and second data 116, 118 may be performed by one or more converter 120 as previously described, which may be part of the digital coach 100 or may be part of the server 80 on which the digital coach 100 is housed. In some embodiments, the device(s) 30 or interactive device 13 may convert the first and second data 116, 118 prior to transmission to the digital coach 100. In some embodiments, the first and second data 116, 118 do not need to be converted, or only some of the data must be converted to be used by the digital coach 100.

With reference to FIGS. 9A and 9B, semantically analyzing and interpreting the first and second data, as at 280, may further include comparing the first and second data to level definitions, as at 310. The level definitions 148 are as previously described, and may first be modified, as at 311, to adjust the level definitions for a patient's medical history, lifestyle, or other information. Semantically analyzing, as at 280, further includes classifying the first and second data based on the level definitions, as at 312. The level definitions 148 and classifications are described above in greater detail. Analysis may further include generating assessment(s) of first and second data based on the classifications, as at 314. Generating the assessments may occur by combining the data with the classification to create a new string of digital information known as an assessment, such as "a blood pressure reading of 160/70 is high for most people, but is normal for this person." Other examples can be found in the discussion above. These steps may occur in the analyzer 130 of the processor 110, as depicted in FIG. 7, although other computational structures may be capable of performing these steps as well.

As shown in FIGS. 9A and 9B, the analysis continues with comparing first and second data to first data, second data, and semantic information of predefined interpretations in the knowledge base, as at 320. As described above, semantically related information 162 may be information that is related to certain data by context or correlation, as may be described or defined in the knowledge base(s) 145.

The method continues with forming a series of candidate interpretations based on the first and second data, as at 322. These candidate interpretations 165 are as described above. The method then includes prioritizing the candidate interpretations 165 based on similarity to the predefined interpretations, as at 324. Prioritizing the candidate interpretations 165 may include be based on context, correlation, statistical probability, weighting, algorithm, equation, or other similar method. The method continues with selecting a primary interpretation from the candidate interpretations, as at 325. In at least one embodiment, this primary interpretation 168 will be the one that most closely matches or has the highest degree of similarity to a predefined interpretation 166.

In some embodiments, the method may include identifying the appropriate rule to apply rule based on the interpretations. Various rules 149 are available in the memory 140, and may apply to either the assessment 135, semantic information 162 or the entire interpretation 165. Rules that apply to the entire interpretation 165 may be more appropriate than other rules applying only to subsets or parts thereof. The appropriateness of a rule may be based on a statistical analysis, weighting, algorithm, equation, or other similar method.

The method continues with generating at least one action based on the primary interpretation, as at 326. As described above this action(s) may preferably be ones that correspond with the predefined interpretation 166 that best matches the primary interpretation 168. In other embodiments, the action (s) is generated by applying the rule to the interpretation. This process is described in greater detail above, and may include applying "if, then" rules or machine learning systems to the interpretations 165 to interpret the data and provide next steps.

The resulting action(s) 167 may be executed, as at 328. This may include selecting a subsequent script and presenting it to the user, as at 330; sending operative instruction(s) to the device(s), as at 332; sending a notification to the HSP, as at 334; sending an update to the patient record, as at 335; and sending an alert to a third party, as at 336. These are just some possible actions that may be executed. Any action or instruction discussed above with respect to each recipient 180 may be executed here as actions. The action(s) may be executed through the I/O 82 and through the network 20 or Internet to the appropriate entity 180.

In other embodiments, the actions may be ranked or prioritized according to which is the most likely to be correct, which can be adapted over time to become more accurate, and the the highest ranked or prioritized action 167 of the available actions is selected, as discussed above.

The method continues, gathering additional first and second data 116, 118 as necessary until the goal of the session or interaction is achieved. For instance, once it is established that the patient is on track or there is nothing further to check, the interaction or session may end.

Since many modifications, variations and changes in detail can be made to the described preferred embodiments, it is intended that all matters in the foregoing description and shown in the accompanying drawings be interpreted as illustrative and not in a limiting sense. Thus, the scope of the invention should be determined by the appended claims and their legal equivalents. Now that the invention has been described,

What is claimed is:

1. A system for facilitating a synthetic interaction between a user and a computer-implemented program, said system comprising:
   an interactive device associated with the user, said interactive device configured to present a preselected script to the user through at least one of video and audio display, said interactive device further configured to collect and transmit first data responsive to said preselected script from the user, said first data being at least one of spoken words, written text and motion, said interactive device further configured to selectively collect and transfer second data from at least one peripheral device;
   said at least one peripheral device configured to collect and transmit said second data, said second data being indicative of at least one physiological condition of the user as detected by said at least one peripheral device and further being at least one of quantitative and qualitative measurements;
   a digital coach in electronic communication with said interactive device and said at least one peripheral device, said digital coach comprising:
   a) a memory including a knowledge base having at least one of:
      i. first level definitions defining categories relating to said first data, each of said first level definitions defined by predefined first reference points;
      ii. second level definitions defining categories relating to said second data, each of said second level definitions defined by predefined second reference points;
      iii. a plurality of predefined interpretations of known information relating to said first data and second data;
      iv. semantic information including medical information correlating certain ones of said first data with certain ones of said second data;

v. at least one rule having instructions for operation to said first and second data and further having at least one associated action; and vi. predefined actions corresponding to at least one of said predefined interpretations and said at least one rule; and b) an analyzer in electronic communication with said memory and at least one of said interactive device and said at least one peripheral device, said analyzer configured to:

i. receive said first data from said interactive device and said second data from one of said interactive device and said at least one peripheral device;

ii. compare said first data to said predefined first reference points;

iii. create a first assessment by combining said first data with category information of one of said first level definitions based on said predefined first reference points;

iv. compare said second data to said predefined second reference points;

v. create a second assessment by combining said second data with category information of one of said second level definitions based on said predefined second reference points;

c) an action engine having a processor in electronic communication with said memory, said analyzer and at least one of said interactive device and said at least one peripheral device, said action engine configured to:

i. select said preselected script and instruct said interactive device to present said preselected script to the user;

ii. receive said first assessment and said second assessment from said analyzer;

iii. semantically expand said first assessment and said second assessment into at least one candidate interpretation, said at least one candidate interpretation being a string of at least two related ones of said first data assessment, said second data assessment, said first data, said second data, and said semantic information;

iv. compare said at least one candidate interpretation to said predefined interpretations stored in said knowledge base and select a primary interpretation from said at least one candidate interpretations through the application of one of:

A. said at least one rule having at least one associated action, said at least one rule selected from at least one candidate rule through the application of an operator selected from the group consisting of:
1. Statistical analysis,
2. weighting,
3. algorithm, and
4. equation; and B. an operator identifying the highest degree of similarity between said at least one candidate interpretation and said predefined interpretations selected from the group consisting of:
1. Statistical analysis,
2. weighting,
3. algorithm, and
4. equation;

v. generate at least one action for said selected primary interpretation according to one of:

A. said predefined action corresponding to said predefined interpretation to which said selected primary interpretation has the highest degree of similarity; and B. applying said at least one rule to said selected primary interpretation; and vi. execute said at least one action for said selected primary interpretation, said at least one action including instructing said interactive device to present a subsequent script to the user.

2. The system as recited in claim 1, wherein said synthetic interaction includes an identified goal, and wherein said action engine is further configured to:

(vii) select and instruct said interactive device to present a subsequent script to the user to seek additional first data;

(viii) send an operative instruction to said at least one peripheral device to collect additional second data;

(ix) receive additional first assessment and additional second assessment from said analyzer; and (x) repeat steps (iii) through (vi) on said additional first and second assessments until an identified goal of said synthetic interaction is achieved.

3. The system as recited in claim 1, wherein one of said actions includes selecting said subsequent script to present to said user based on said primary interpretation.

4. The system as recited in claim 1, wherein said interactive device is selected from the group consisting of a personal computer, laptop, tablet, mobile device, smart device, phone, watch, and speaker device.

5. The system as recited in claim 1, wherein said at least one peripheral device is a medical device.

6. The system as recited in claim 1, wherein said preselected script includes at least one of a sentence, a paragraph, a demonstration, a question, a response, and a command.

7. The system as recited in claim 1, wherein each of said first level definitions and said second level definitions present a different level of risk.

8. The system as recited in claim 7, wherein said knowledge base further includes modification rules that modify at least one of said first level definitions and said second level definitions.

9. The system as recited in claim 1, wherein each of said first level definitions and said second level definitions are one of quantitative and qualitative.

10. The system as recited in claim 1, wherein said knowledge base includes a plurality of modules each having information specific to a distinct topic and all of said modules being relevant to the particular user of said system.

11. The system as recited in claim 10, wherein said topics of each of said modules are one of disease-specific, condition-specific, user-specific, lifestyle, and health.

12. The system as recited in claim 10, wherein each of said modules including a plurality of predefined scripts each relating to the topic of said corresponding module.

13. The system as recited in claim 12, wherein certain ones of said predefined scripts are cross-referenced in different ones of said modules.

14. The system as recited in claim 12, wherein certain ones of said predefined scripts are grouped into series within a corresponding one of said modules, each series being a different sub-topic related to and within said topic of said corresponding one of said modules.

15. The system as recited in claim 1, further comprising a machine learning system in electronic communication between said processor and said memory, said machine learning system facilitating analysis of said first and second data by at least one of said analyzer and said action engine.

16. The system as recited in claim 1, further comprising at least one of:
(i) a computing device associated with a health service provider, said computing device in electronic communication with said processor and said memory, wherein said at least one knowledge base includes treatment protocol provided by said computing device associated with said health service provider, said action engine further configured to send at least one of an alert, a notification of status, a notification of an exception, an appointment scheduling request, and a prescription request to said computing device associated with said health service provider according to said at least one action;
(ii) a patient record in electronic communication with said processor, said patient record including at least one of an electronic health record and an electronic medical record, said action engine configured to access information from said patient record and update said patient record according to said at least one action; and
(iii) a computing device associated with a third party, said computing device in electronic communication with said processor, said action engine configured to send at least one of an alert, a preselected script, at least one of said first and second data, a request for an ambulance, a request for prescription refill, a status request, and a lab results request to said computing device associated with a third party according to said at least one action.

17. A method of analyzing data, comprising:
(i) receiving first data from an interactive device associated with a user, said first data being at least one of spoken words, written text and motion;
(ii) receiving second data from one of said interactive device and at least one peripheral device, said second data collected by said at least one peripheral device, indicative of a physiological condition of said user, and being at least one of qualitative and quantitative measurements;
(iii) comparing said first data to predefined first reference points defining first level definitions;
(iv) creating a first assessment by combining said first data with category information of one of said first level definitions based on said predefined first reference points;
(v) comparing said second data to predefined second reference points;
(vi) creating a second assessment by combining said second data with category information of one of said second level definitions based on said predefined second reference points;
(vii) semantically expanding said first assessment and said second assessment into at least one candidate interpretation being a string of at least two related ones of said first data assessment, said second data assessment, said first data, said second data, and semantic information;
(viii) comparing said at least one candidate interpretation to predefined interpretations stored in said knowledge base, (v) selecting a primary interpretation from said at least one candidate interpretation through the application of one of:
  A. at least one rule stored in said knowledge base and having at least one associated action, said at least one rule selected from at least one candidate rule through the application of an operator selected from the group consisting of:
    1. Statistical analysis,
    2. weighting,
    3. algorithm, and
    4. equation; and
  B. an operator identifying the greatest degree of similarity between said at least one candidate interpretation and said predefined interpretations selected from the group consisting of:
    1. Statistical analysis,
    2. weighting,
    3. algorithm, and
    4. equation;
(vi) generating at least one action for said primary interpretation according to one of:
  A. said predefined action corresponding to said predefined interpretation to which said selected primary interpretation has the highest degree of similarity based upon said predefined actions from said knowledge base; and
  B. applying said at least one rule to said selected primary interpretation; and
(vii) executing said at least one action for said primary interpretation including instructing said interactive device to present a subsequent script to the user.

18. The method as recited in claim 17, further comprising selecting and instructing said interactive device to present a subsequent script to the user to seek additional first data; sending an operative instruction to said at least one peripheral device to collect additional second data; receiving said additional first assessment additional second assessment from said analyzer; and repeating steps (iii) through (vii) on said additional first and second assessments until said identified goal of said synthetic interaction is achieved.

19. The method as recited in claim 18, further comprising modifying at least one of said first level definitions and said second level definitions and creating at least one of said first assessment and said second assessment based on said modified level definitions.

20. The method as recited in claim 17, further comprising sending at least one of (i) at least one of an alert, a notification of status, a notification of an exception, an appointment scheduling request, and a prescription request to a computing device associated with said health service provider; (ii) an update to a patient record; and (iii) at least one of an alert, a preselected script, at least one of said first and second data, a request for an ambulance, a request for prescription refill, a status request, and a lab results request to a computing device associated with a third party.

* * * * *